United States Patent [19]

Holfert et al.

[11] Patent Number: 4,981,484
[45] Date of Patent: Jan. 1, 1991

[54] MODIFIED ELLIPTICAL ARTIFICIAL HEART

[76] Inventors: John W. Holfert, 109 W. 2700 So., Bountiful, Utah 84010; Don B. Olsen, 803 N. 300 W. St. Marks Bldg., Salt Lake City, Utah 84103

[21] Appl. No.: 438,810

[22] Filed: Nov. 20, 1989

Related U.S. Application Data

[63] Continuation-in-part of Ser. No. 232,384, Aug. 15, 1988.

[51] Int. Cl.$^5$ .............................................. A61M 1/10
[52] U.S. Cl. .......................................... 623/3; 600/16
[58] Field of Search ........................ 623/3; 600/16, 17

[56] References Cited

U.S. PATENT DOCUMENTS

| | | | |
|---|---|---|---|
| 4,144,595 | 3/1979 | Unger | 623/3 |
| 4,397,049 | 8/1983 | Robinson et al. | 623/3 |
| 4,588,404 | 5/1986 | Lapeyre | 600/17 X |
| 4,838,889 | 6/1989 | Kolff | 623/3 |
| 4,863,461 | 9/1989 | Jarvik | 623/3 |

FOREIGN PATENT DOCUMENTS 764681  9/1980  U.S.S.R. .................. 623/3

*Primary Examiner*—Ronald Frinks
*Attorney, Agent, or Firm*—Thorpe, North & Western

[57] ABSTRACT

An artificial heart device for producing heart pumping action as part of a total artificial heart implant comprising a housing of elongate configuration enclosing a pumping volume of sufficient capacity to provide adequate blood flow within the living being. A deformable diaphragm structure is attached at its perimeter to an interior housing surface approximately at the largest perimeter of the pumping volume to form a deformable partition deviding the pumping volume into a blood chamber and a drive chamber. The diaphragm structure has a modified hemi-ellipsoidal configuration when fully extended, modification being represented by four sections of substantially equal quadrants formed by intersection of the diaphragm structure with two orthogonal planes oriented in parallel relationship with the vertical axis. The curvature of each medial section of each quadrant is reduced or flattened to form a medial section having a lower profile as compared to surrounding ellipsoidal curvature. This structure reduces occurrence of bi-axial folding and enhancing random folding activity within the diaphragm. Valve inlet and outlet means are coupled to the housing in communication with the blood flow chamber for attachment along with the circulatory system of a living being. Pumping means are provided for actuating alternating extension and collapse of the diaphragm structure with respect to the drive chamber to simulate pumping action of the natural heart.

16 Claims, 3 Drawing Sheets

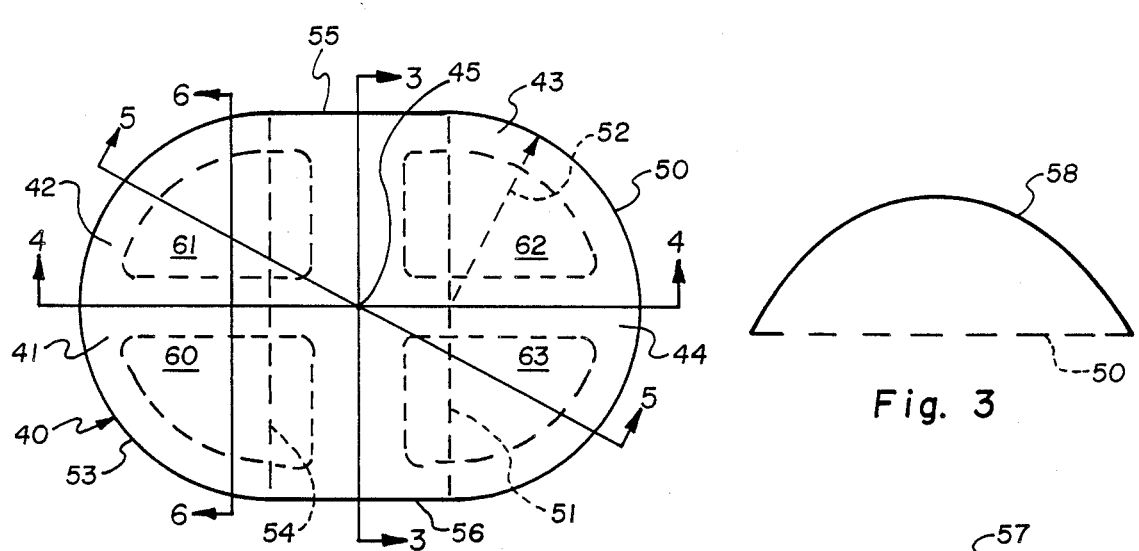
Fig. 2
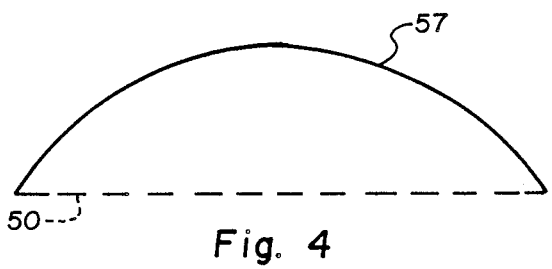
Fig. 3
Fig. 4
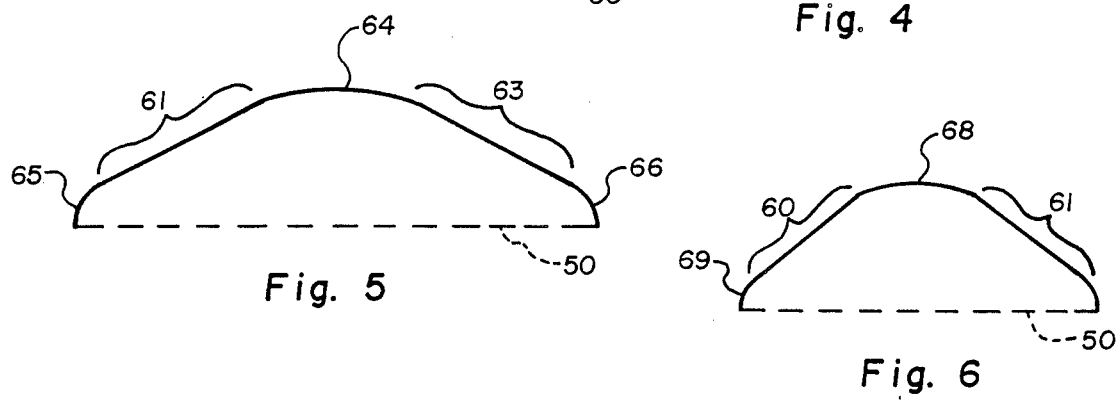
Fig. 5
Fig. 6
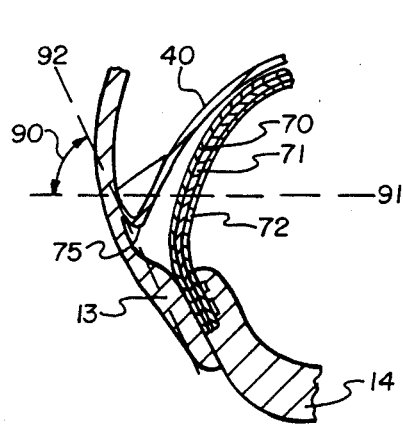
Fig. 7
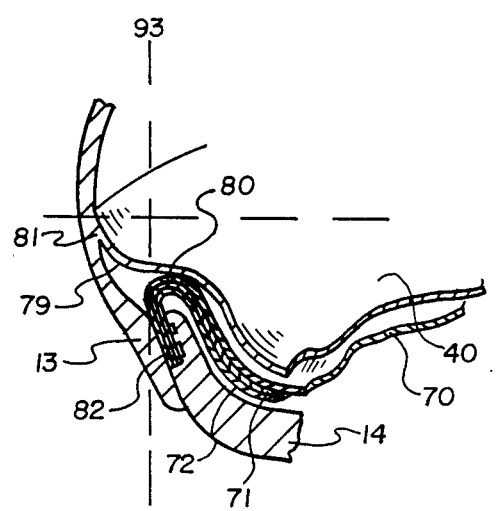
Fig. 8

MODIFIED ELLIPTICAL ARTIFICIAL HEART

This application is a continuation-in-part of a parent application Ser. No. 07/232,384, filed Aug. 15, 1988 and entitled "Elliptical Artificial Heart."

BACKGROUND OF THE INVENTION

1. Field of Invention:

This invention pertains to an artificial heart device for implantation within the chest cavity of a living being. More particularly, it relates to a total artificial heart which includes a semi-rigid shell construction having an internal compartment divided into a blood chamber and a pumping chamber which are separated by a flexible diaphragm.

2. Prior Art:

The successful long term operation of a total artificial heart embodying a blood chamber and a pumping chamber depends on the survivability of the intermediate flexible diaphragm. Over its expected lifetime, the flexible diaphragm will extend and collapse many millions of times to provide the desired pumping action for blood through the total artificial heart. Many factors contribute to mechanical failure of the flexible diaphragm, usually characterized by splitting or other loss of structural integrity. Obviously, the failure of the flexible diaphragm results in failure of the pumping system, which may be fatal to a dependent patient.

A prior application filed under the title of "Elliptical Artificial Heart" discloses the use of multiple diaphragms including a blood diaphragm whose interior surface defines part of the blood containing compartment, and one or more pumping diaphragms which operate to collapse and extend the blood diaphragm to activate pumping action. These pumping diaphragms may be activated by pneumatic negative/positive pressure, or may be effected by a hydraulic fluid flow system operable under similar principles.

One of the major directions of research to control diaphragm survivability has been to develop predictable compositions with minimal elastic memory such that the folding patterns within the diaphragm become random. Failure to develop a random folding pattern results in a localized fold, which upon repeated folding movement, can weaken the localized diaphragm area. Accordingly, diaphragm compositions have included polyurethanes, Cardiothane TM, Lycra TM and other materials whose elastic character enhances random folding patterns rather than repeated folding at the same location.

It has been discovered that even the best of compositions will ultimately succumb to material failure if localized folding of the diaphragm occurs a sufficient number of times. Ultimately, the molecular structure becomes weak following repeated similar folding at the same location. Once the molecular structure weakens, the diaphragm will favor folding at the weaker position, thereby aggravating the tendency of the diaphragm to continually fold at one location.

Particular locations of the diaphragm are very susceptible to recurring folding patterns, leading to diaphragm failure. One specific area of vulnerability is the peripheral edge of the diaphragm. A second area of common folding problem occurs because of the suction applied upon negative pressure through the pumping chamber. In prior art devices, pressure gradients within the pumping chamber would tend to favor specific diaphragm fold locations. Typically, these pressure gradients were most intense near the inlet opening for the pumping fluid. In very early embodiments, the diaphragm itself would be sucked into the inlet, creating abnormally high stress at that portion of the diaphragm.

What is needed is a diaphragm system which is better adapted to generate random folding patterns, and patterns which are not likely to create mechanical failure within the diaphragm structure. Not only is the primary diaphragm surface area of concern, but also the periphery structure where the diaphragm is attached to the interior housing of the total artificial heart compartment.

OBJECTS AND SUMMARY OF THE INVENTION

It is an object of the present invention to provide a total artificial heart wherein the diaphragm structure develops random folding patterns which prevent the development of localized weakness at any specific area of the diaphragm structure.

A further object of the present invention is to provide a diaphragm whose fold patterns tend to be uni-axial, as opposed to bi-axial folds.

A still further object of this invention is to develop an improved method of attachment of the diaphragm within the total artificial heart housing to prevent stress from being applied at the juncture of the diaphragm and interior housing surface.

Yet another object of this invention is to provide a total artificial heart wherein the pumping system reduces the imbalance of stress applied to the diaphragm by developing uniform pumping pressures across the diaphragm surface.

These and other objects are achieved in a total artificial heart comprising a housing of approximate elliptical configuration enclosing a pumping volume of sufficient capacity to sustain adequate blood flow within a living being during operation and wherein the housing is substantially symmetrical about its short or vertical axis. A deformable diaphragm structure is attached at its periphery to an interior housing surface approximately at the largest perimeter of the pumping volume about the vertical axis. This diaphragm forms a deformable partition which divides the interior housing into a blood chamber and a pumping chamber. The diaphragm structure is adapted with a modified hemi-ellipsoidal configuration wherein a fully extended position at the end of either systole or diastole. This modified hemi-ellipsoidal configuration favors a uni-axial fold in contrast to prior art bi-axial fold patterns. The modified hemi-ellipsoidal configuration is characterized by quadrants formed by intersection with the diaphragm structure of two orthogonal planes oriented in colinear relationship with the vertical axis, one plane intercepting across the short width of the housing and the other plane intercepting along the long width. Each quadrant of the diaphragm is configured with substantial ellipsoidal curvature adjacent the intercepting planes; however, said curvature is reduced toward the medial section of each quadrant to form a medial section of lower profile as compared to an ellipsoidal curvature.

Valve inlet and outlet means are provided through the housing to permit flow of blood to and from the blood chamber and for attachment in line with the circulatory system of a living being. Such configuration corresponds to a flow configuration comparable to one of the two ventricles of a natural heart. Pumping means for actuating alternating extension and collapse of the diaphragm structure with respect to the pumping chamber in a recurring pumping manner are also provided.

Other objects and features of the present invention will be apparent to those skilled in the art, based on the following detailed description, taken in combination with the accompanying drawings.

DESCRIPTION OF DRAWINGS

FIG. 2 shows a graphic top view of a diaphragm structure, having the base of the structure outlined at its perimeter.

FIG. 3 shows a cross sectional view of the diaphragm structure taken along the lines 3—3.

FIG. 4 shows a cross sectional view of the diaphragm structure taken along the lines 4—4.

FIG. 5 shows a cross sectional view of the diaphragm of FIG. 2, taken along the lines 5—5.

FIG. 6 shows a cross sectional view of FIG. 2, taken along the lines 6—6.

FIG. 7 shows an embodiment of the present diaphragm structure attached at an interior face of the total artificial heart compartment when in the systole stage of pumping.

FIG. 8 shows the structure illustrated in FIG. 7 in the opposing position during diastole.

DETAILED DESCRIPTION OF THE INVENTION

Referring now to the drawings

Figure 1:
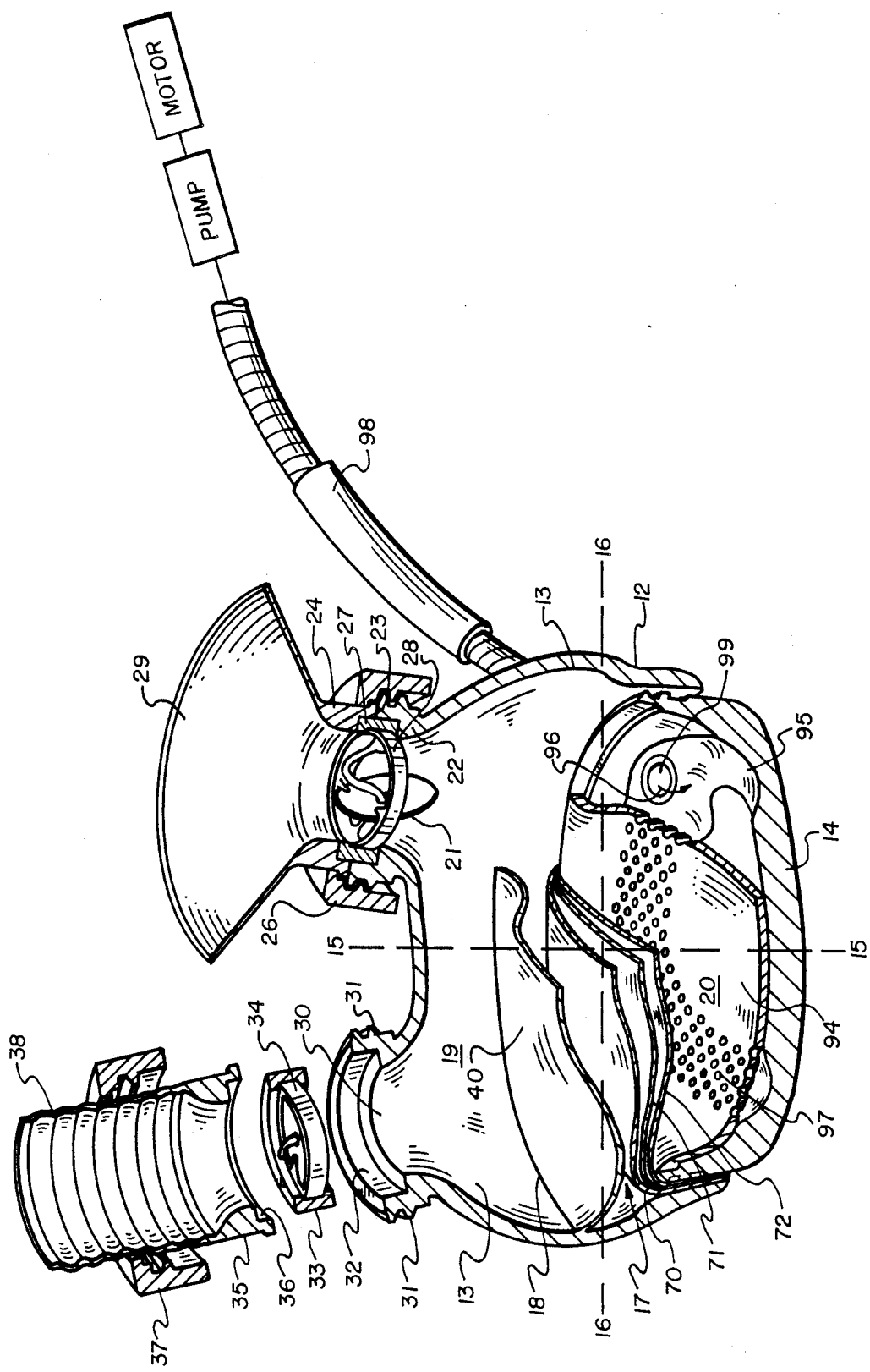
FIG. 1 shows a partial cut-away view of a total artificial heart constructed in accordance with the principles of the present invention.

FIG. 1 shows an artificial heart device for producing heart pumping action as part of a total artificial heart implant. This device could be used as either a left or right ventricle, or two could be used for total heart implantation. The heart includes a ventricle housing. This ventricle housing includes an interior surface 13 which extends down to a base 14 enclosing the lower portion of the ventricle housing.

The interior volume of the ventricle (also referred to as the pumping volume) is to be of sufficient capacity to sustain adequate blood flow within a living being during its operation. The following shows a set of representative dimensions for an artificial ventricle having a stroke volume of 100 cubic centimeters.

|  | Left | Right |
| --- | --- | --- |
| Stroke volume | 107 cc | 107 cc |
| Displacement Volume | 215 cc | 218 cc |
| Height (external) | 2.395" | 2.405" |
| Width (external) | 2.660" | 2.660" |
| Length (external) | 3.770" | 3.770" |
| Diaphragm Height (internal) | 0.880" | 0.880" |

In the present embodiment, the housing 12 and attached base 14 are generally symmetrical about a vertical axis 15 assuming an imaginary position centrally located with respect to the ventricle. A contrasting horizontal axis 16 is also represented.

A deformable diaphragm structure 17 is attached at its perimeter 18 to the interior housing surface 13 of the ventricle. The location of attachment is approximately at the largest perimeter of the pumping volume about the vertical axis, substantially dividing the internal housing into two near equal compartments. These compartments are identified as a blood chamber 19 representing that portion of the internal housing above the diaphragm structure 17, and a pumping or drive chamber 20, comprising that portion of the housing below the diaphragm structure 17. Blood enters the blood chamber 19 through an inlet port 21 which is enclosed by a housing connector ring 22. This is locked in abutting contact 23 with an atrial cuff connector ring 24. This locked configuration is accomplished by means of a screw connector ring 26 which pulls the respective atrial cup connector end 24 and housing connector ring 22 into tight fit. These two members 22 and 24 sandwich a valve insert 27 and attached valve 28. An attached atrial cuff 29 provides the means for suturing directed to the atrium of the human being for in-line flow with the circulatory system.

Blood outflow passes through an outlet 30 and within a heart and connector ring 31 as with the previously mentioned housing connector ring 22, and an annular channel 32 is formed to receive a valve insert 33 and attached valve 34. This valve insert 33 is sandwiched between the housing connecting ring 31 and a graft connector ring 35, which has a corresponding annular channel 36 to permit the valve to nest therein. These two connector rings 31 and 35 are locked together by a screw connector ring 37. Graft material 38 is coupled to the graft connector ring 35 and provides a suture location for attachment to the pulmonary artery or other flow connection with the circulatory system. The illustrated connector ring/valve systems disclosed for the inlet and outlet ports of the present embodiment are more fully described in a pending U.S. patent application filed on May 18, 1987 under Ser. No. 07/051,578 and entitled "Tubular Interconnect Device for Use Within The Circulatory System."

The primary feature of the present invention involves the utilization of a uniquely designed diaphragm structure 17 which is configured to minimize folding stress in the diaphragm during operation. This is accomplished by effective design within the diaphragm structure itself, as well as at the peripheral attachment 18 and with respect to the holding chamber 20. Each of these features will be discussed in greater detail hereafter.

For example, the present invention incorporates a novel diaphragm configuration generally described as a hemiellipsoidal configuration. The geometrical configuration of this design is set forth in FIG. 2, which shows an isolated member of the diaphragm structure 17 in top view. In actuality, this member is the blood diaphragm 40 which is adapted at its interior with blood compatible surface structure and is joined at its periphery 18 in a seamless construction (despite the graphic representation of a connecting line at point 18).

The illustrated diaphragm 40 (FIG. 2) is divided into four substantially equal quadrants 41, 42, 43 and 44. These are the same quadrants which would be formed by intersection of two orthogonal planes represented by lines 3—3 and 4—4 which are oriented in parallel relationship and are colinear with the vertical axis 45, which would be colinear with vertical axis 15 in FIG. 1. Line 3—3 is considered co-planar with the short plane, meeting that plane extending across the short width of the housing. Line 4—4 corresponds to location of the long plane, corresponding to that plane extending along the length of the elongate diaphragm structure.

To clarify the structure of the diaphragm illustrated in FIG. 2, perimeter line 50 represents the perimeter of the diaphragm base. The modified semi-ellipsoidal structure projects upward from this base 50 in configurations as illustrated in FIGS. 3 through 6. The base geometry comprises a semi-circle extending to line 51 and having a radius 52. A second, opposing semi-circle of similar size exists as identified as 53, and extends to broken line 54. The two line segments 55 and 56 represent parallel lines which join the two semi-circle halves to the single, elongated structure. Accordingly, this represents the baseline configuration of the modified ellipse, as viewed from the vertical axis 45.

In contrast, the hemi-ellipsoid configuration is seen in FIGS. 3 and 4. FIG. 4 shows an ellipsoidal curve extending along the line plane 4—4 and is identified as item 57. The base line 50 corresponds to the base perimeter illustrated in FIG. 2 as item 50. FIG. 3 shows the ellipsoidal configuration taken along the cross section 3—3 and as identified as item 58. Without modifications as described hereafter, the upward projecting diaphragm 40 could accurately be described as a substantially hemi-ellipsoidal configuration, modified by the elongated structure of the base line 50.

To reduce the occurrence of bi-directional folds and to enhance random collapse of the diaphragm structure, modifications are made to the geometries of each of the four quadrants 41, 42, 43 and 44. The modified areas of surface geometry are identified within dashed lines representing medial sections 60, 61, 62 and 63. The modification made generally consists of reducing the curvature within this medial section to thereby reduce or lower the profile as compared to an actual ellipsoidal curvature. This is illustrated in FIG. 5, which is taken along the line 5—5 of FIG. 2. Here again, the base line is represented by base line 50 and the upper curved line represents the curvature of the projecting diaphragm structure as it is extended during either systole or diastole. This curved line represents the path shown by line 5—5, which extends from opposing perimeter of locations at line 50 through the vertical axis 45. It is apparent that this path intercepts central sections 61 and 63. These sections represent a reduced curvature or lower profile as is shown in FIG. 5. The top section of curve 64 corresponds to an ellipsoidal curve similar to FIG. 4, item 57. Similarly, the lower ends of the side segments 65 and 66 correspond to actual ellipsoidal curves similar to those at the side structure of FIG. 4.

Similarly, FIG. 6 shows a cross section taken along the lines 6—6 and disclose flattened sections 60 and 61, with the intermediate ellipsoidal curve of 68. Here again, lateral ellipsoid curve continues at 69.

In summary, it has been discovered that by reducing the curvature or flattening the structure within approximate areas identified as central sections in each of the four quadrants of the ellipsoidal structure, bi-directional folding is reduced and uni-directional folding is enhanced. This has been shown to greatly reduce the stress applied to any given segment of the diaphragm structure and thereby greatly increase the life expectancy of the structure as it reciprocates in pumping action. The amount of curvature reduction may vary; however, it should be sufficient to develop a predominant uni-axial fold pattern as compared with a bi-axial fold pattern within the respective diaphragm quadrants. As can be seen by the side views in FIGS. 5 and 6, these middle sections 60, 61 and 62 and 63 are substantially flat, compared to the curvature of the remaining surface structure in ellipsoidal form.

It will be noted in FIG. 1 that most of the diaphragms are utilized to divide the blood chamber 19 from the pumping chamber 20. The blood diaphragm 40 has already been described in detail. The present embodiment utilizes a multiple set of diaphragms including intermediate diaphragms 70 and 71 and air diaphragms 72. As with the blood diaphragm 40, pumping diaphragm 70, 71 and 72 also can be configured in a hemi-ellipsoidal geometry with modified medial sections in a somewhat flattened condition. These respective diaphragms should also be lubricated between each layer.

The second means of reducing stress within the diaphragm during pumping action is to provide an attachment of the diaphragm at the interior wall 13 in a roll-sock configuration. The object of this structural attachment is to insure that the extreme extended configurations during systole and diastole, some amount of roll exists at the periphery of each diaphragm. Maintenance of such roll prevents stress from being applied at the juncture 18 where the diaphragm is attached to the interior surface 13. By eliminating such stress, mechanical failure of the diaphragm structure is substantially reduced.

FIG. 1 illustrates a configuration of the respective diaphragms approximately one-half way through pumping cycle when the diaphragms are in a half extended position. It will be noted that folding action within the diaphragm is generally represented as uni-axial, thereby reducing localized stress which often occurs with a bi-axial fold. The roll-sock configuration is maintained around the periphery of the diaphragm structures, thereby eliminating stress at the points of attachment.

FIG. 7 shows the same diaphragm structure extended at full systole. It should be noted that the roll-sock configuration 75 is maintained at the blood diaphragm, as well as some roll being maintained in the air diaphragm 70, 71 and 72. FIG. 8 illustrates the opposing extension of the diaphragm during diastole. In this case, nominal roll 79 is maintained in the blood diaphragm, and the maximum roll-sock configuration 80 occurs with the air diaphragm. The nominal role 79 is provided when the blood diaphragm is attached to the interior housing face near connection point 81 such that it projects toward a lower half of a vertical axis within a range of $-1$ to $-80$ degrees with respect to a plane containing the long axis 93. A more preferred range as illustrated in FIG. 8 occurs where the blood membrane projects and approximately $-40$ to $-75$ degrees. As has been previously indicated, the attachment of this blood membrane at connecting perimeter 81 is in the configuration of a seamless blood contacting surface for the interior of the blood chamber. In both instances, stress is prevented from being applied at the connection points 81 and 82.

The foregoing structure is placed in operation by a pumping means (FIG. 1) which actuates alternating extension and collapse of the diaphragm structure with respect to the drive or pumping chamber. This sequence occurs in recurring pumping manner to alternately expel and infuse blood from and to the blood chamber in a manner comparable to the pumping action of a natural heart. This pumping means includes a pumping motor for increasing or decreasing fluid pressure (not shown), which is coupled through a flow line 98 to an opening 99 within the pumping chamber. In prior art structures, openings similar to 99 were unshielded from the pumping diaphragms and therefore resulted in greater pressure at the opening 99, with a decreasing pressure gradient extending the increased distance from the opening. In this configuration, the pumping diaphragm mirrors the greater pressure of the opening 99 tends to respond more quickly and becomes a localized area of vending or holding action. Repetition of this sequence over millions of cycles tends to weaken that localized area nearest the fluid opening 99.

Figure 9:
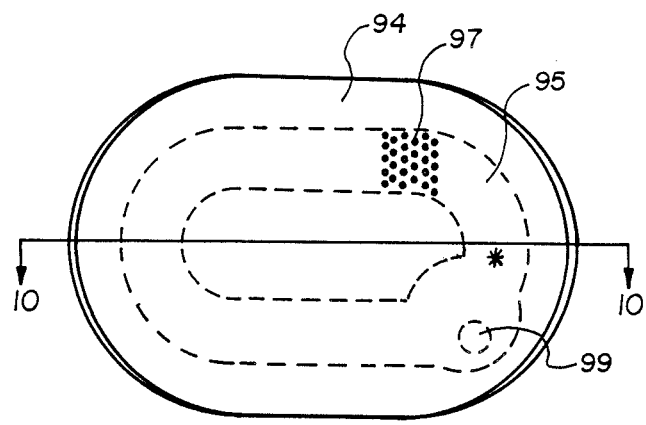
FIG. 9 shows a top view of the base structure and pumping screen of the subject total artificial heart.
Figure 10:
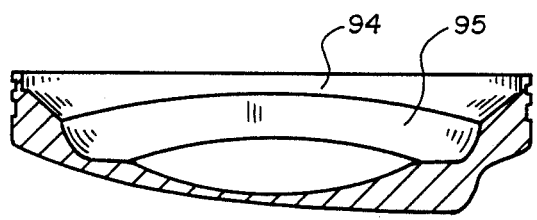
FIG. 10 shows a cross section of FIG. 9, taken along the lines 10—10, deleting the pumping screen.

In the present embodiment, the base member of 14 includes an air passage channel 95 shaped in annular configuration (FIG. 9). The fluid opening 99 forms part of that channel and supplies positive or negative pressure throughout the pumping chamber by virtue of fluid flow along that channel.

A shield 94 is adhered to a top surface of the base member and includes an annular or other configurational array of small openings 97 which allow passage of the fluid between the channel 95 and pumping chamber 20. Although FIG. 1 shows only a portion of the base member 14 covered, in actuality the full base member is covered by this shield 94. Therefore as positive or negative pressure is induced into the pumping chamber through opening 99, its effect is disposed through the flow channel 95 and through adjacent small openings 97 which communicate to the pumping chamber 20. Localized stress is thereby prevented, having a more uniform application of pressure is applied across the pumping diaphragm 72. The illustrated holes 97 are formed by a number 70 drill in an offset pattern to enhance uniform distribution of fluid flow from the flow channel.

It will be apparent to those skilled in the art that the foregoing description of specific embodiments and examples is not to be considered limiting, except by the following claims.

We claim:

1. An artificial heart device for producing heart pumping action as part of a total artificial heart implant, said device comprising:
   a housing of elongate configuration enclosing a pumping volume of sufficient capacity to sustain adequate blood flow within a living being during operation, said housing being substantially symmetrical about its short axis (also referred to as a vertical axis of the housing);
   a deformable diaphragm structure attached at its perimeter to an interior housing surface approximately at the largest perimeter of the pumping volume about the vertical axis to form a deformable partition dividing the pumping volume into a blood chamber and a drive chamber, said diaphragm structure having a modified hemi-ellipsoidal configuration when fully extended at end of either systole or diastole;
   said modified hemi-ellipsoidal configuration being characterized by four substantially equal quadrants formed by intersection with the diaphragm structure of two orthogonal planes oriented in parallel relationship with the vertical axis, one plane intersecting across the short width of the housing (referred to as the short plane), the other plane intersecting along the long width (referred to as the long plane), each quadrant of the diaphragm structure being configured with substantial ellipsoidal curvature adjacent the intersecting planes, said curvature being reduced toward the medial section of each quadrant to form a medial section of lower profile as compared to an ellipsoidal curvature;
   valved inlet and outlet means coupled through the housing in communication with the blood chamber for attachment in line with the circulatory system of the living being and in a flow configuration comparable to one of the two ventricals of a natural heart;
   pumping means for actuating alternating extension and collapse of the diaphragm structure with respect to the drive chamber in a recurring pumping manner to alternately expel and infuse blood from and to the blood chamber in a manner comparable to the pumping action of a natural heart.

2. An artificial heart device as defined in claim 1, wherein a base perimeter of the diaphragm comprises a substantially parallel middle section parallel with the long axis of the housing, said parallel middle section merging with semi-circular sections at each end of the diaphragm.

3. An artificial heart device as defined in claim 1, wherein the diaphragm structure comprises a plurality of membrane layers joined individually at their periphery to the interior housing surface at separated perimeter locations, one membrane comprising a blood membrane and being exposed at its interior face to the blood chamber, another membrane comprising a pumping membrane having its exterior face exposed to the pumping chamber.

4. An artificial heart device as defined in claim 3, wherein the blood membrane is attached to the interior housing face such that it projects toward a lower half of the vertical axis within a range of minus 1 to minus 80 degrees with respect to a plane containing the long axis.

5. An artificial heart device as defined in claim 4, wherein the pump membrane is attached to the interior housing face such that it projects approximately parallel with the vertical axis to develop a roll at the pump membrane periphery when in a collapsed position.

6. An artificial heart device as defined in claim 5, further comprising a plurality of pumping membranes in stacked configuration.

7. An artificial heart device as defined in claim 6, wherein the blood membrane projects at approximately $-40$ to $-75$ degrees.

8. An artificial heart device as defined in claim 4, wherein the blood membrane is configured as a seamless blood contacting surface for the interior of the blood chamber.

9. An artificial heart device as defined in claim 1, wherein diaphragm structure near the diaphragm perimeter is attached to the interior housing surface and is configured in size and shape to maintain a roll therein when extended to its alternate extreme position during systole and diastole, thereby substantially eliminating stress at the perimeter of attachment to the interior surface.

10. An artificial heart device as defined in claim 1, wherein the diaphragm is configured in an elliptical cross-section at the intersection of the short plane therewith.

11. An artificial heart device as defined in claim 10, wherein the housing is configured in an elliptical cross-section at the intersection of the long plane therewith.

12. An artificial heart device as defined in claim 1, wherein the amount of curvature reduction is determined by development of predominant uniaxial fold patterns as compared with biaxial fold patterns within the diaphragm quadrant structures as it reciprocates during systole and diastole.

13. An artificial heart device as defined in claim 1, wherein the medial section of each of the diaphragm quadrants is substantially flat.

14. An artificial heart device as defined in claim 1, wherein the means for actuating pumping action of the diaphragm structure comprises a pneumatic pumping system.

15. An artificial heart device as defined in claim 1, wherein the means for actuating pumping action of the diaphragm structure comprises a hydraulic pumping system.

16. An artificial heart device as defined in claim 1, wherein the housing further includes a base member which closes off a bottom portion of the housing, said base member having an interior surface including an annular channel formed to provide a path for fluid flow at part of the pumping means, said base member further comprising a diaphragm support screen integrally attached at the interior surface of the base member to provide a support surface to the diaphragm during diastole, said screen including an annular array of small openings positioned over the annular channel to enable fluid flow to the pumping chamber.

* * * * *